United States Patent [19]
Kotani et al.

[11] Patent Number: 4,725,541
[45] Date of Patent: Feb. 16, 1988

[54] PROCESS FOR PRODUCING L-HISTIDINE BY FERMENTATION

[75] Inventors: Yukinobu Kotani; Kuniki Kino, both of Hofu, Japan

[73] Assignee: Kyowa Hakko Kogyo Co., Ltd., Japan

[21] Appl. No.: 583,378

[22] Filed: Feb. 24, 1984

[30] Foreign Application Priority Data

Feb. 25, 1983 [JP] Japan ................... 58-30481

[51] Int. Cl.$^4$ ................... C12P 13/24; C12N 1/20; C12R 1/15
[52] U.S. Cl. ................... 435/107; 435/253; 435/843
[58] Field of Search ............... 435/107, 253, 840, 843, 435/68, 243, 244

[56] References Cited

U.S. PATENT DOCUMENTS 3,676,301 7/1972 Nakajima et al. ................... 435/107
3,713,977 1/1973 Nakayama et al. ................. 435/107
4,495,283 1/1985 Araki et al. ........................ 435/107

FOREIGN PATENT DOCUMENTS 7005692 1/1982 Japan ................... 435/107
0193695 11/1983 Japan ................... 435/107

OTHER PUBLICATIONS

Frunzio et al, *Proc. Natl. Acad. Sci.*, vol. 78(5), pp. 2767–2771, May 1981, "In Vivo and in Vitro Detection of the Leader RNA of the Histidine Operon of *Escherichia coli* K–12".

Bruni et al, *J. Bacteriology*, vol. 142(1), pp. 32–42, Apr. 1980, "Structure and Physiological Studies of the *Escherichia coli*, Histidine Operon Inserted into Plasmid Vectors".

Grisolia et al, *J. Bact.*, vol. 142(1), pp. 692–700, Aug. 1982, "Cloning and Expression of the Distal Portion of the Histidine Operon of *Escherichia coli* K–12".

*Primary Examiner*—Thomas G. Wiseman
*Assistant Examiner*—Robin Lyn Teskin
*Attorney, Agent, or Firm*—Antonelli, Terry & Wands

[57] ABSTRACT

L-histidine is produced by culturing, in a nutrient medium, an L-histidine producing mutant microorganism belonging to the genus Corynebacterium. The mutant is resistant to a precursor for ubiquinone biosynthesis. L-histidine is accumulated in the culture liquor and is recovered therefrom.

4 Claims, No Drawings

PROCESS FOR PRODUCING L-HISTIDINE BY FERMENTATION

BACKGROUND OF THE INVENTION

The present invention relates to a process for producing L-histidine by fermentation, and more specifically to a process for producing L-histidine by culturing an L-histidine producing mutant microorganism belonging to the genus Corynebacterium in a nutrient medium and recovering the L-histidine produced thereby. The mutants employed are endowed with a resistance to a precursor for ubiquinone biosynthesis.

L-histidine is an important amino acid which is commercially useful as a food additive or medicament. Accordingly, it is an object of the present invention to provide an improved process for production of such amino acid on an industrial scale at low cost.

Heretofore, it has been known that histidine analog-resistant strains belonging to the genus Corynebacterium have an ability to produce a significant amount of L-histidine (U.S. Pat. No. 3,713,977). Attempts to increase the productivity of these L-histidine producing microorganisms by imparting additional properties to them have also been made. For example, a process using strains endowed with a resistance to a purine analog or a pyrimidine analog is proposed in Japanese Published Examined Patent Application No. 18798/1977.

A further process using strains endowed with a resistance to sulfa drugs is disclosed in Japanese Published Unexamined Patent Application No. 49490/1975. Yet another process using strains endowed with a resistance to 5-methyltryptophane, α-amino-β-hydroxyvaleric acid, imidazole or aminotriazole is proposed in Japanese Published Unexamined Patent Application No. 49491/1975.

Although the processes exemplified above result in improved yields of L-histidine, the production yields of such processes, nevertheless, are comparatively low from a commercial application standpoint. Thus, a need exists for a process for producing L-histidine in higher yields at low cost.

To this end, it has now been found that L-histidine productivity of an L-histidine producing microorganism belonging to the genus Corynebacterium is greatly improved when such microorganism is endowed with a resistance to a precursor for ubiquinone biosynthesis. Heretofore, it was not recognized that the productivity of L-histidine could be improved by endowing an L-histidine producing microorganism with such trait.

SUMMARY OF THE INVENTION

In accordance with the present invention, L-histidine is produced by culturing an L-histidine producing mutant microorganism belonging to the genus Corynebacterium in a nutrient medium until L-histidine is accumulated in the culture liquor and thereafter recovering said L-histidine, wherein the mutant is characterized by a resistance to a precursor for ubiquinone biosynthesis.

As used herein the term "precursor for ubiquinone biosynthesis" means that the precursor is a biosynthetic intermediate of ubiquinone which plays an important role in the electron transport of respiratory chain for acquiring the energy.

DESCRIPTION OF THE INVENTION

The microorganism utilized in the present invention is a mutant belonging to the genus Corynebacterium which has the ability to produce L-histidine and which has been endowed with a resistance to a precursor for ubiquinone biosynthesis. A suitable mutant may be obtained by using a mutant inherently having an ability to produce L-histidine (for example, histidine analog-resistant strains and sulfa drug-resistant strains) or an improved mutant thereof as a parent strain and imparting a resistance to at least one precursor for ubiquinone synthesis, e.g. p-hydroxycinnamate (p-coumarate) and its fluoride, o-hydroxycinnamate (o-coumarate) and its fluoride, m-hydroxycinnamate (m-coumarate) and its fluoride, phenyl pyruvate, p-hydroxyphenyl pyruvate and its fluoride, phenyl acetate, p-hydroxyphenyl lactate and its fluoride, cinnamate, benzoate, p-hydroxybenzoate and its fluoride, and p-hydroxybenzaldehyde and its fluoride.

Alternatively, a suitable mutant may be prepared by a reverse process, i.e. by imparting the above-mentioned ability to produce L-histidine to a mutant resistant to a precursor for ubiquinone biosynthesis.

The mutant microorganism useful in carrying out the present invention can be obtained by conventional means such as ultraviolet ray irradiation, X-ray irradiation, radioactive ray irradiation and a treatment with chemical mutagens. A treatment using N-nitro-N'-methyl-N-nitrosoguanidine (hereinafter referred to as NTG) is preferably employed.

As the strain used in this invention, a mutant having other properties such as various nutrient requirements, drug resistance, drug sensitivity and drug dependence in addition to a combination of the above properties may be employed.

Strains mutated as mentioned above are screened by culturing in a nutrient medium and a strain having the ability to produce L-histidine in greater yields than its parent strain is selected and used in this invention. A specific example of the procedure for obtaining a suitable strain is given in the following description with reference to a mutant belonging to the genus Corynebacterium.

Procedure

Corynebacterium glutamicum ATCC 21607 is mutated in a conventional manner using NTG and strains resistant to a precursor for ubiquinone biosynthesis are selected using conventional technique. The cells of the strains are suspended in M/20 phosphate buffer solution (pH 7.0). To the suspension is added 200 μg/ml NTG and the mixture is maintained at 30° C. for 30 minutes. The treated mutants are collected and washed with the same buffer solution. Then, the mutants are spread on a medium (pH 6.8) comprising 3% glucose, 0.2% urea, 10 ppm each of Fe, Mn and Cu ions, 1 mg/l thiamine hydrochloride, 50 μg/l biotin, 2% agar and 2 mg/ml p-hydroxycinnamate. Culturing is carried out at 30° C. for 2 to 10 days.

Among these mutants, those having a significantly improved ability of producing L-histidine are separated. Representative strain among the thus obtained mutants was named CPCA-1349.

In a similar manner, Corynebacterium glutamicum CPCA-3946, a p-hydroxycinnamate-resistant mutant was prepared from Corynebacterium glutamicum NRRL B-15045 having an L-histidine producibility.

The aforesaid Corynebacterium glutamicum CPCA-1349 and Corynebacterium glutamicum CPCA-3946 mutants were deposited on Feb. 19, 1983 with the Fermentation Research Institute, the Agency of Industrial Science and Technology, Japan as FERM P-6919 and 6920 respectively. The deposits were converted to the deposits under the Budapest Treaty and the corresponding international deposit numbers are FERM BP-485 and FERM BP-486 respectively. They are available therefrom under the terms of the Budapest Treaty.

As the medium used for the culturing step of the invention, either a natural medium or synthetic medium may be employed as long as it contains assimilable carbon sources, nitrogen sources and inorganic materials as well as small quantities of other nutrients which may be required by the specific mutant used. Typical additional nutrients are those employed in the following examples.

As a suitable carbon source, carbohydrates such as sucrose, fructose, glucose, maltose, mannose, starch, starch hydrolyzate, molasses, etc.; sugar alcohols such as glycerine, sorbitol, etc.; organic acids such as formic acid, acetic acid, lactic acid, fumaric acid, malic acid, etc.; lower alcohols such as ethanol, methanol, etc., and the like may be employed. These carbon sources may be employed either alone or as a mixture at various weight ratios. The total amount may be initially supplied in the medium or may be supplied by incremental addition.

As the nitrogen source, ammonia, inorganic and organic ammonium salts such as ammonium chloride, ammonium sulfate, ammonium carbonate, ammonium acetate, ammonium nitrate, ammonium phosphate, etc.; urea; natural nitrogen containing substances such as peptone, meat extract, corn steep liquor, casein hydrolyzate, soybean meal hydrolyzate, etc. and the like may be employed.

As the inorganic materials, potassium dihydrogen phosphate, dipotassium hydrogen phosphate, magnesium sulfate, sodium chloride, ferrous sulfate, manganese sulfate, calcium carbonate, etc. are employed.

When the strain used requires nutrients such as amino acids, nucleic acids, vitamins, and the like, it is, of course, also necessary to add appropriate amounts of these substances to the medium. In some cases, such nutrients may be supplied by another medium component and thus specific supplementation is not required.

Culturing is generally carried out at 20°–40° C., under aerobic conditions, for example, by shaking culture or aeration agitation culture until recoverable quantities of L-histidine is produced in the culture liquor, usually within 1–8 days. After the completion of culturing, L-histidine is recovered from the culture liquor by a conventional method such as ion exchange resin treatment or the like.

Practice of certain specific embodiments of the invention is illustrated by the following representative examples.

EXAMPLE 1

In this example, Corynebacterium glutamicum CPCA 1349, CPCA 3946, ATCC 21607 and NRRL B-15045 were employed as seed strains. The seed strains were cultured with shaking in a medium having a composition of 4 g/dl glucose, 2 g/dl polypeptone, 0.5 g/dl yeast extract, 0.15 g/dl KH$_2$PO$_4$, 0.05 g/dl K$_2$HPO$_4$, 0.05 g/dl MgSO$_4$.7H$_2$O, 50 μg/l biotin and 0.3 g/dl urea (pH 7.2) at 30° C. for 24 hours. Then, 1 ml of the resulting seed culture was transferred to a 300 ml-Erlenmeyer flask containing 20 ml of a fermentation medium comprising 10 g/dl glucose, 0.5 g/dl meat extract, 4 g/dl (NH$_4$)$_2$SO$_4$, 0.15 g/dl KH$_2$PO$_4$, 0.05 g/dl K$_2$HPO$_4$, 0.05 g/dl MgSO$_4$.7H$_2$O, 1 mg/l thiamine hydrochloride, 10 mg/l FeSO$_4$.7H$_2$O, 10 mg/l MnSO$_4$.4-6H$_2$O, 1 mg/l CuSO$_4$.5H$_2$O, 0.3 g/dl urea, 100 μg/l biotin and 3 g/dl CaCO$_3$ (pH 7.4) and cultured with shaking at 30° C. for 4 days. The amount of L-histidine produced and the yield based on sugar are shown in Table 1.

TABLE 1

| Strain | L-Histidine (g/l) | Yield based on Sugar (%) |
|---|---|---|
| ATCC-21607 | 5.1 | 5.1 |
| CPCA-1349 | 11.2 | 11.2 |
| NRRL B-15045 | 16.8 | 16.8 |
| CPCA-3946 | 20.4 | 20.4 |

EXAMPLE 2

The same procedures as described in Example 1 were repeated except that 10 g/dl molasses (calculated as glucose) was used in place of glucose of the fermentation medium. The results are shown in Table 2.

TABLE 2

| Strain | L-Histidine (g/l) | Yield based on Sugar (%) |
|---|---|---|
| ATCC-21607 | 4.8 | 4.8 |
| CPCA-1349 | 10.7 | 10.7 |
| NRRL B-15045 | 16.3 | 16.3 |
| CPCA-3946 | 19.8 | 19.8 |

What is claimed is:

1. A biologically pure culture of *Corynebacterium glutamicum* having the identifying characteristics of FERM BP-485, which produces recoverable quantities of L-histidine when cultured.

2. A biologically pure culture of *Corynebacterium glutamicum* having the identifying characteristics of FERM BP-486, which produces recoverable quantities of L-histidine when cultured.

3. A process for producing L-histidine by fermentation which comprises culturing an L-histidine producing mutant microorganism having the identifying characteristics of *Corynebacterium glutamicum* FERM BP-485 and having a resistance to p-hydroxycinnamate and an enhanced productivity of L-histidine compared with that of parent strain in a nutrient medium until L-histidine is accumulated in the culture liquor and thereafter recovering said L-histidine therefrom.

4. A process for producing L-histidine by fermentation which comprises culturing an L-histidine producing mutant microorganism having the identifying characteristics of *Corynebacterium glutamicum* FERM BP-486 and having a resistance to p-hydroxycinnamate and an enhanced productivity of L-histidine compared with that of parent strain in a nutrient medium until L-histidine is accumulated in the culture liquor and thereafter recovering said L-histidine therefrom.

* * * * *